United States Patent

Micetich et al.

[11] 4,039,530
[45] Aug. 2, 1977

[54] THIOAMIDES

[75] Inventors: Ronald G. Micetich; Robert B. Morin, both of Edmonton, Canada

[73] Assignee: Connlab Holdings Limited, Willowdale, Canada

[21] Appl. No.: 589,560

[22] Filed: June 23, 1975

[51] Int. Cl.² .......................................... C07D 205/08
[52] U.S. Cl. .................................. 260/239 A; 544/17
[58] Field of Search ................................... 260/239 A

[56] References Cited

U.S. PATENT DOCUMENTS 3,275,626  9/1966  Morin .............................. 260/239 A

FOREIGN PATENT DOCUMENTS 2,303,889  1/1973  United Kingdom

OTHER PUBLICATIONS

Kamiya et al., I, Tet. Letters 3001 (1973).
Kamiya et al., II, Abstracts—4th Int. Cong. of Heterocyclic Chemistry, p. 97 (1973).
Kamiya et al. III, C. A. 80, 82619x (1973).
Bonchandon et al., Chem. Abs. 83, 43355a (1975).
Allan et al., J. Chem. Soc. Perkins I, 1182 (1973).
Barton et al., Chem. Comm, 1137 (1971).

*Primary Examiner*—Donald G. Daus
*Assistant Examiner*—Mark L. Berch
*Attorney, Agent, or Firm*—Weiser, Stapler & Spivak

[57] ABSTRACT

The invention relates to compounds of the formula:

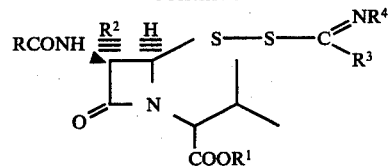

-continued wherein
  R stands for lower alkyl, aryl, heteroaryl, benzyl, heteroaryloweralkyl, phenoxyloweralkyl, phenylthioloweralkyl, 4-amino-1-butyl and suitably protected derivatives, α-aminobenzyl and protected derivatives such as the carbamates (benzyl, trichloroethyl and methoxymethyl) and aldehyde and ketone adducts, α-hydroxybenzyl and protected derivatives, α-carboxybenzyl and protected derivatives, α-sulfobenzyl and protected derivatives, the radical $R^5O-$, $R^5S-$, or $R^5R^6N-$,
    wherein $R^5$ and $R^6$ may be the same or different and each be taken from the group lower alkyl, aryl, aryloweralkyl and heteroaryl and additionally, in the case of $R^5R^6N-$, $R^5$ and/or $R^6$ may be hydrogen;
  $R^1$ is hydrogen or a cleavable radical such as loweralkoxymethyl, acyloxymethyl, loweralkylthiomethyl, loweralkyl, 2,2,2-trichloroethyl, benzyl, substituted (nitro, methoxy or halo) benzyl, benzhydryl, phenacyl or trialkylsilyl;
  $R^2$ is hydrogen or methoxy;
  $R^3$ stands for lower alkyl, aryl, aryloweralkyl, heteroaryl, and the radicals $R^5O-$, $R^5S-$, $R^5R^6N-$, or $R^5R^6NR^7N-$ wherein $R^5$ and $R^6$ have the same meaning set forth above; and $R^7$ has the same meaning as $R^5$ or $R^6$ including hydrogen, and
  $R^4$ has the same meaning as $R^5$ or $R^6$ including hydrogen.

Broken lines at positions 3 and 4 in the formula indicate a double bond in either of the two positions;

The novel compounds are useful intermediates in the preparation of cephalosporins and penicillins.

14 Claims, No Drawings

THIOAMIDES

In copending application Ser. No. 589,561 filed June 23, 1975 there is disclosed novel azetidinone imidoyldisulfides which are useful as intermediates for preparing 3-iodocephams which are themselves useful in preparing certain cephalosporin derivatives.

The azetidinone imidoyldisulfides prepared in accordance with the present invention correspond to the general formula:

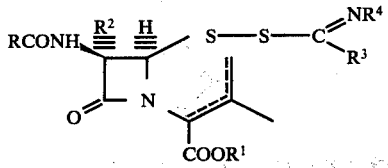

which is taken to also represent the two double bond isomers:

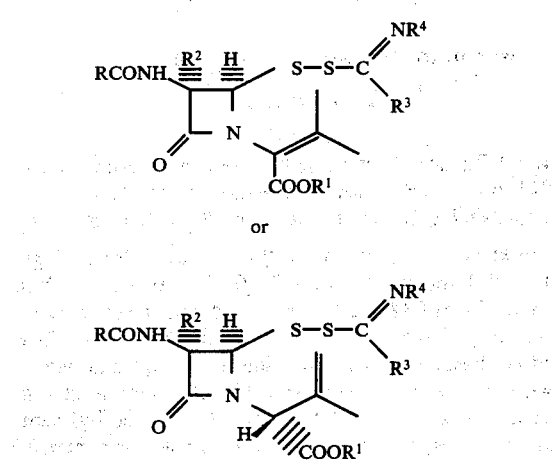

In the above formula:

R stands for lower alkyl, aryl, heteroaryl, benzyl, heteroaryl lower alkyl, phenoxyloweralkyl, phenylthioloweralkyl, 4-amino-1-carboxy-1-butyl and suitably protected derivatives. α-aminobenzyl and protected derivatives such as the carbamates (benzyl, trichloroethyl and methoxymethyl) and aldehyde and ketone adducts, α-hydroxybenzyl and protected derivatives, α-carboxybenzyl and protected derivatives, α-sulfobenzyl and protected derivatives, $R^5O—$, $R^5S—$, $R^5R^6N—$, wherein $R^5$ and $R^6$ may be the same or different and each be taken from the group lower alkyl, aryl, arylloweralkyl and heteroaryl, and in the case where R stands for $R^5R^6N—$, $R^5$ and/or $R^6$ may be hydrogen;

$R^1$ is hydrogen or a cleavable radical such as loweralkoxymethyl, acyloxymethyl, loweralkylthiomethyl, lower alkyl, 2,2,2-trichloroethyl, benzyl, substituted (nitro, methoxy or halo)benzyl, benzhydryl, phenacyl, or trialkylsilyl;

$R^2$ is hydrogen or methoxy;

$R^3$ stands for lower alkyl, aryl, arylloweralkyl, heteroaryl, $R^5O—$, $R^5S—$, $R^5R^6N—$, or $R^5R^6NR^7N—$, wherein $R^5$ and $R^6$ have the same meaning as set forth above; and $R^7$ has the same meaning as $R^5$ or $R^6$ including hydrogen, and $R^4$ has the same meaning as $R^5$ or $R^6$ including hydrogen.

The novel azetidinone imidoyldisulfides are prepared by heating a penicillin sulfoxide (either the α- or β-sulfoxides or a mixture can be used) of the formula;

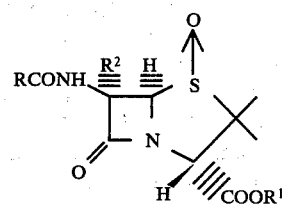

wherein R, $R^1$ and $R^2$ are as previously defined, with a thioamide of the formula;

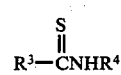

wherein $R^3$ and $R^4$ are as previously defined.

The reaction is carried in the presence of a suitable inert solvent such as for example dioxane or toluene. As an example of suitable thioamides, there may be mentioned thioacetamide thiobenzamide, thiourea, thiosemicarbazide, thiocarbamates and dithiocarbamates.

The reaction temperature and time required for the reaction is determined by the nature of the penicillin sulfoxide 2, and the thioamide 3. Reaction temperatures of 80° to 130° have been found convenient, and times of 3 to 5 hours. It is desirable to remove the water formed in the reaction, by azeotropic distillation or by the use of a Dean-Stark trap, or the use of drying agents such as a molecular sieve or magnesium sulfate.

The nature of the products formed is determined by the nature and purity of the penicillin sulfoxides 2, the thioamide 3, and the solvent used, the temperature and time of reaction, and the presence of impurities. The conjugate isomer 1a, is favoured by the presence of base and by extended reaction times, and 1b can be converted to 1a on treatment with a suitable base such as triethylamine.

The azetidinone disulfides 1, are useful intermediates and can be converted by known processes to penicillins and cephalosporins.

Thus, for example, the azetidinone disulfides 1b, on treatment with an iodinating agent such as iodine and sulfenyl iodides, are converted to the respective 2-iodomethylpenams or the 3-iodocephams and these compounds are converted to cephalosporins by known processes.

The 3-iodocephams when treated with a base such as pyridine or picoline or collidine, undergo dehydroiodination to form the ceph-3-ems, which are used for the preparation of the commercially important cephalexin.

EXAMPLES

The present invention will be more readily understood by referring to the following examples which are given only to illustrate the invention rather than limit its scope.

EXAMPLE 1

2-Oxo-3-Phenoxyacetamido-4-Acetimidoyldithio-α-Isopropenylazetidin-1-Acetic Acid, 1b, (R = φOCH$_2$CO-NH—, R$^1$ = H, R$^3$ = CH$_3$, R$^4$ = H)

A mixture of anhydrous penicillin V sulfoxide (0.36 g., 0.001 mole, prepared by heating the hydrate to constant weight at 60° C under vacuum over P$_2$O$_5$), and thioacetamide (0.08 g., ~0.001 mole) in purified dioxane (25 ml) was heated under reflux with stirring for 5 hrs in an oil-bath kept at 120°. The clear reaction mixture was concentrated under vacuum to give a brown foam. The ir spectrum (CHCl$_3$): 3350, 1775, 1680, 1600 cm$^{-1}$ and nmr spectrum (CDCl$_3$): signals at δ8.4, 8.0 (NH's and —COOH), multiplet at 7.5 to 6.9 (C$_6$H$_5$), signals at 5.68 (β-lactam Hs), 5.22.

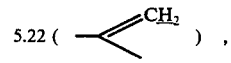

4.95 (—CHCOOH), 4.62 (—CH$_2$),

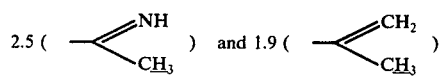

are in agreement with the assignment.

EXAMPLE 2

Methyl 2-Oxo-3-Phenoxyacetamido-4-Acetimidoyldithio-α-Isopropenylazetidin-1-Acetate, 1b (R = φOCH$_2$CONH, R$^1$ = CH$_3$, R$^2$ = H, R$^3$ = CH$_3$, R$^4$ = H) and Methyl Penicillin V A mixture of methyl penicillin V sulfoxide (0.38 g., 0.001 mole) and thioacetamide (0.08 g., 0.001 mole) in purified dioxane (25 ml) was heated under reflux with stirring for 5 hrs, in an oil bath maintained at 120° C. The clear reaction mixture was concentrated under vacuum to a brown foam. The ir spectrum (CHCl$_3$) showed strong sharp singlets at 1780, 1745, and 1700 cm$^{-1}$ with weaker absorptions at 1600 and 3400 cm$^{-1}$. The nmr spectrum (CDCl$_3$) indicated a mixture containing methyl 2-oxo-3-phenoxyacetamido-4-acetimidoyl-dithio-α-isopropenylazetidin -1-acetate, 1b, as the main product characterized by signals at δ5.22 and 5.1

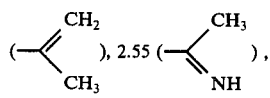

and 1.92

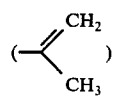

among others, and methyl penicillin V (estimated at 20% and confirmed by thin layer chromatography characterized by its gem-dimethyl signals at δ1.65 and 1.5. In addition, there were trace amounts of methyl 4-phenoxyacetamidoisothiazol-3-one -1-α-isopropenylacetate, characterized by its signals at ca. δ9.2 and 8.83.

EXAMPLE 3

2-Oxo-3-Phenoxyacetamido-4(N-Phenylacetimidoyl)-Dithio-α-Isopropenylazetidin-1-Acetic Acid, 1b (R = φOCH$_2$CONH, R$^1$ = H, R$^2$ = H, R$^3$ = CH$_3$, R$^4$ = φ)

A mixture of anhydrous penicillin V sulfoxide (0.36 g., 0.001 mole) and thioacetanilide (0.15 g., 0.001 mole) in purified dioxane (25 ml) was heated under reflux with stirring for 5 hrs in an oil bath kept at 120°. The clear reaction mixture was concentrated under vacuum to a brown foam. The ir spectrum (CHCl$_3$): 3350, 1775, 1680, 1600 cm$^{-1}$ and nmr spectrum (CDCl$_3$): signals at δ10.25, 8.2 to 6.95 (m, C$_6$H$_5$, NH and COOH), 5.65 (β-lactam protons),

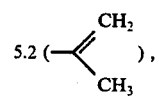

4.95 (CHCOOH), 4.6 (—O—CH$_2$—),

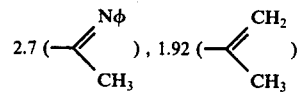

are consistent for the assigned structure.

EXAMPLE 4

Methyl 2-Oxo-3-Phenoxyacetamido-4-(N-Phenylacetimidoyl)-Dithio-α-Isopropenylazetidin-1-Acetate, 1b (R = φOCH$_2$CONH, R$^1$ = CH$_3$, R$^2$ = H, R$^3$ = CH$_3$, R$^4$ = φ)

A mixture of methyl penicillin V sulfoxide (0.38 g., 0.001 mole) and thioacetanilide (0.15 g., 0.001 mole) in purified dioxane (25 ml) was heated under reflux with stirring for 5 hrs in an oil bath kept at 120° C. The clear reaction mixture on concentration under vacuum gave a brown foam. The nmr spectrum (CDCl$_3$) indicated that the reaction was incomplete, about 20% of methyl penicillin V sulfoxide being present, along with methyl 2-oxo-3-phenoxyacetamido-4-(N-phenylacetimidoyl)-dithio-α-isopropenylazetidin-1-acetate characterized by δ5.7 to 5.3 (m, β-lactam protons), 5.2 and

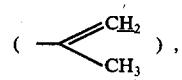

4.92 (-CHCOOCH$_3$), 4.5 (-O-CH$_2$-), 5.05

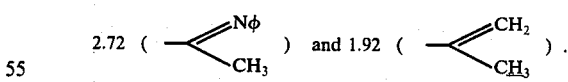

In a similar manner using solvents such as toluene, dichloroethane, mesitylene, and thioamides such as thiobenzamide, N-methylthioacetamide, N-methylthiobenzamide, N-phenylthiobenzamide, thionicotinamide, thioisonicotinamide, 2-thiazolethioacetamide and 2-thiazolethiobenzamide, and penicillin sulfoxides such as trichlorethyl penicillin V sulfoxide, methoxymethyl penicillin V sulfoxide, p-nitrobenzyl penicillin V sulfoxide, penicillin G sulfoxide, methoxymethyl penicillin G sulfoxide, trichlorethyl penicillin G sulfoxide, 6-phenoxyamidopenicillin sulfoxide, methoxymethyl N-(methoxymethyloxycarbonyl)ampicillin sulfoxide, di(- methoxymethyl)-carbenicillin sulfoxide, and 6-thien-2-ylacetamido-6-methoxypenicillin sulfoxide: various azetidinone disulfides of formula 1 are obtained.

EXAMPLE 5

Methyl 2-Oxo-3-Phenoxyacetamido-4-(Aminoimidoyl)Dithio-αIsopropenylazetidin-1-Acetate, 1b (R = φOCH$_2$CONH, R$^1$ = CH$_3$, R$^2$ = H, R$^3$ = NH$_2$, R$^4$ = H)

A mixture of methyl penicillin V sulfoxide (0.2 g., 0.00052 moles) and thiourea (0.04 g., 0.000052 moles) in purified dioxane (15 ml) with one drop of dimethylaniline was heated under reflux with stirring for 5 hrs in an oil bath kept at 120° C. The reaction mixture on concentration under vacuum gave a brown foam. The nmr and ir spectra of the foam indicated the presence of the desired compound. The ir spectrum showed strong absorptions at 1775, 1740, 1700 and 1600 cm$^{-1}$.

EXAMPLE 6

Methyl 7-Phenoxyacetamido-3-Methyl-3-Iodocepham-4-Carboxylate from Methyl 2-Oxo-3-Phenoxyacetamido-4-(Aminoimidoyl)Dithio-α-Isopropenylazetidin-1-Acetate, 1b (R = φOCH$_2$CONH, R$^1$ = CH$_3$, R$^2$ = H, R$^3$ = NH$_2$, R$^4$ = H)

The total crude product obtained in Example 5 was dissolved in methylene chloride (5 ml) and stirred with iodine (0.13 g., 0.00052 moles) at ambient temperature for 16 hrs. The reaction mixture was then concentrated to give a brown foam. The formation of methyl 7-phenoxyacetamido-3-methyl-3-iodocepham-4-carboxylate in this reaction was shown by comparing the nmr spectrum of the crude product with that of an authentic sample. A thin layer chromatogram using an authentic sample of the 3-iodocepham confirmed its presence in the reaction mixture.

EXAMPLE 7

Dehydroiodination of Methyl 7-Phenoxyacetamido-3-Methyl-3-Iodocepham-4-Carboxylate Using Pyridine in Benzene A solution of methyl 7-phenoxyacetamido-3-methyl-3-iodocepham-4-carboxylate and pyridine in benzene was heated under reflux, in an oil-bath maintained at 90°. Periodically aliquots of the reaction mixture were removed and the progress of the reaction followed by analysing the nmr spectrum of the residue. The 3-iodocepham in the mixture is characterized by the C$_4$-H singlet at δ4.9, the C$_6$-H doublet at δ5.38 and the C$_2$-CH$_2$ quartet at δ2.95; the ceph-3-em is characterized by its C$_6$-H doublet at δ5.05 and its C$_2$-CH$_2$ doublet at δ3.35. Any ceph-2-em produced is easily detected by its C$_3$-CH$_3$ singlet at δ1.92 and its C$_2$-H signal at δ6.1. In all our experiments using pyridine as the base there were no detectable amounts of the ceph-2-em isomer produced. The following table summarizes the results of experiments in which the relative amount of pyridine was varied.

TABLE 1

Dehydroiodination of 3-Iodocepham Using Pyridine In Benzene

| No. | Mole Ratio of Pyridine | | Time of Reflux | Yield of Ceph-3-em (%)* |
|---|---|---|---|---|
| 1. | 2.5 | equivalents | 0.5 hr | 45 |
| 2. | 2.5 | " | 1.0 hr | 60 |
| 3. | 2.5 | " | 1.5 hr | 67 |
| 4. | 5.0 | equivalents | 0.5 hr | 50 |
| 5. | 5.0 | " | 1.0 hr | 66 |
| 6. | 5.0 | " | 1.5 hr | 80 |
| 7. | 5.0 | " | 3.0 hr | ~100 |
| 8. | 10 | equivalents | 0.5 hr | 60 |
| 9. | 10 | " | 1.0 hr | ~100 |
| 10. | 10 | " | 1.5 hr | 100 |

*There was no detectable trace of any ceph-2-em isomer in any of these experiments.

We claim:
1. The novel azetidinone imidoyldisulfides of the formula:

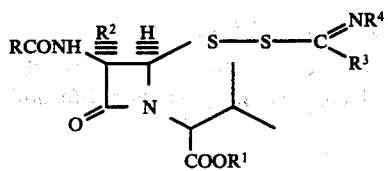

wherein R is loweralkyl, phenyl, benzyl, 4-amino 1-carboxy-1-butyl, phenoxyloweralkyl, phenylthioloweralkyl, alpha-hydroxybenzyl, alpha-carboxybenzyl, alpha-sulfobenzyl, alpha-aminobenzyl and protective derivatives thereof selected from the group consisting of N-benzyloxycarbonyl, N-trichloroethyoxycarbonyl and N-methoxymethyl carbonyl, and R$^5$O—, R$^5$S—, or R$^5$R$^6$N—
wherein R$^5$ and R$^6$ may be the same or different and each is selected from the group consisting of lower alkyl, phenyl, phenylloweralkyl and when R is R$^5$R$^6$N—, R$^5$ and R$^6$ can also be hydrogen.
R$^1$ is hydrogen or a cleavable radical selected from the group consisting of loweralkoxymethyl, lower alkylthiomethyl, loweralkyl, 2,2,2-trichloroethyl, benzyl, nitrobenzyl, methoxybenzyl and halobenzyl, benzhydryl, and trialkylsilyl;
R$^2$ is hydrogen or methoxy;
R$^3$ is selected from the group consisting of lower alkyl, phenyl, and phenylloweralkyl R$^5$O—, R$^5$S—, R$^5$R$^6$N—, and R$^5$R$^6$NR$^7$N— where R$^5$ and R$^6$ may be the same or different and each is selected from the group consisting of lower alkyl, phenyl, phenylloweralkyl and, where R is R$^5$R$^6$N— R$^5$ and R$^6$ can also be hydrogen and, where R is R$^5$R$^6$NR$^7$N— R$^7$ is the same as R$^5$ and R$^6$ where R$^5$ and R$^6$ are as defined above as including hydrogen;
R$^4$ is selected from the group consisting of loweralkyl, phenyl, phenylloweralkyl and hydrogen.
2. The compound of claim 1, which is 2-oxo-3-phenoxyacetamido-4-acetimidoyldithio-α-isopropenylazetidin-1-acetic acid.
3. The compound of claim 1, which is methyl 2-oxo-3-phenoxyacetamido-4-acetimidoyldithio-α-isopropenylazetidin-1-acetate.
4. The compound of claim 1, which is 2-oxo-3-phenoxyacetamido-4-(N-phenylacetimidoyl)dithio-α-isopropenylazetidin-1-acetic acid.
5. The compound of claim 1, which is methyl 2-oxo-3-phenoxyacetamido-4-(N-phenylacetimidoyl)dithio-α-isopropenylazetidin-1-acetate.

6. The compound of claim 1, which is 2-oxo-3-phenoxyacetamido-4-amidinoyldithio-α-isopropylazetidin-1-acetic acid.

7. The compound of claim 1, which is methyl 3-oxo-3-phenoxyacetamido-4-amidinoyldithio-α-isopropylazetidin-1-acetic acid.

8. The azetidinone of claim 1 wherein $R^1$ is acetoxymethyl.

9. The azetidinone imidoyldisulfides of claim 1 wherein

R is phenoxyloweralkyl, $R^1$ is hydrogen or methyl $R^2$ is hydrogen $R^3$ is methyl or $R^5R^6N-$ where $R^5$ and $R^6$ are hydrogen; and $R^4$ is hydrogen or phenyl.

10. The azetidinones of formula 1, which comprises the isomer being shown by the partial formula

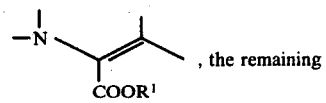, the remaining the remaining portion of the formula being shown in claim 1.

11. The azetidinones of formula 1, which comprises the isomer being shown by the partial formula

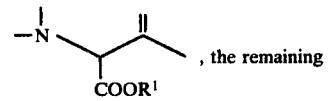, the remaining the remaining portion of the formula being shown in claim 1.

12. The azetidinone of claim 1 wherein $R^3$ is methyl.

13. The azetidinone of claim 1 wherein $R^3$ is amino.

14. The azetidinone of claim 1 wherein $R^4$ is phenyl.

* * * * *